United States Patent [19]

Rubinsztajn

[11] Patent Number: 5,403,909
[45] Date of Patent: Apr. 4, 1995

[54] CATALYSTS FOR POLYCONDENSATION AND REDISTRIBUTION OF ORGANOSILOXANE POLYMERS

[75] Inventor: Slawomir Rubinsztajn, Schenectady, N.Y.

[73] Assignee: General Electric Company, Waterford, N.Y.

[21] Appl. No.: 91,900

[22] Filed: Jul. 15, 1993

[51] Int. Cl.$^6$ ............... C07K 7/10; B01J 31/18; C08G 77/06
[52] U.S. Cl. ........................ 528/20; 528/21; 528/23; 556/453; 556/456; 556/462; 558/153; 558/157; 558/199; 423/300; 502/162; 502/167; 502/200
[58] Field of Search .............. 423/300; 556/453, 456, 556/462; 528/20, 21, 23; 558/153, 157, 199

[56] References Cited

U.S. PATENT DOCUMENTS

| | | | |
|---|---|---|---|
| 2,830,967 | 4/1958 | Nitzsche et al. | 260/46.5 |
| 3,186,967 | 6/1965 | Nitzsche et al. | 260/46.5 |
| 3,839,388 | 10/1974 | Nitzsche et al. | 260/448.26 |
| 4,264,531 | 4/1981 | Li et al. | 558/199 X |
| 4,522,797 | 6/1985 | Pettigrew et al. | 423/300 |
| 4,522,798 | 6/1985 | Lum et al. | 423/300 |
| 4,523,009 | 6/1985 | Neilson et al. | 556/453 X |
| 4,544,536 | 10/1985 | De Jaeger et al. | . |
| 4,551,317 | 11/1985 | Li et al. | 423/300 |
| 4,613,548 | 9/1986 | Lum et al. | 558/199 X |
| 4,725,643 | 2/1988 | Burkkardt | 524/789 |
| 4,780,292 | 10/1988 | Passimourt | . |
| 4,810,480 | 3/1989 | Chambrett et al. | . |
| 4,812,297 | 3/1989 | Passimourt et al. | . |
| 4,888,405 | 12/1989 | Gamon et al. | 528/23 |
| 4,902,490 | 2/1990 | Paginez et al. | . |
| 4,975,510 | 12/1990 | Wegehaupt et al. | 528/21 |
| 5,008,229 | 4/1991 | Schuster et al. | 505/167 |
| 5,101,002 | 3/1992 | Klobucar et al. | 558/199X |
| 5,250,626 | 10/1993 | Landry et al. | 558/199 X |

FOREIGN PATENT DOCUMENTS 2252969 8/1992 United Kingdom .

*Primary Examiner*—Paul F. Shaver

[57] ABSTRACT

Short-chain linear phosphazenes as well as products of their reactions with water, alcohols and organosiloxanes, and the like, are active catalysts for polycondensation and redistribution of organosiloxane polymers.

23 Claims, No Drawings

CATALYSTS FOR POLYCONDENSATION AND REDISTRIBUTION OF ORGANOSILOXANE POLYMERS

This invention relates to short-chain linear phosphazenes as well as products of their reactions with compounds, such as water, alcohols, acids, phenols and organosiloxanes. These compounds are active catalysts for polycondensation and redistribution of organosiloxane polymers.

BACKGROUND OF THE INVENTION

The polycondensation or polymerization of low molecular weight siloxanol oils has been practiced for several years. A wide range of catalysts have been used to perform these processes with reasonable reaction time and temperature. Catalysts that can be used include sulfuric acid, trifluorosulfonic acid, some Lewis acids, sodium hydroxide, potassium hydroxide, tetramethylammonium hydroxide, tetrabutylphosphonium silanolate and some amines. (See, for example, (a) "The Siloxane Bond", Ed. Voronkov, M. G.; Mileshkevich, V. P.; Yuzhelevskii, Yu. A. Consultant Bureau, New York and London, 1978; and (b) Noll, W. "Chemistry and Technology of Silicones", Academia Press, New York, (1968)). A number of patents disclose the preparation and use of linear phosphonitrilic chlorides as catalysts for polycondensation and redistribution of the low viscosity siloxane polymers. In particular, U.S. Pat. No. 2,830,967 (1958), U.S. Pat. No. 3,186,967 (1965), U.S. Pat. No. 3,839,388 (1974), U.S. Pat. No. 4,725,643 (1988), U.S. Pat. No. 4,975,510 (1990) (to Wacker Chemie) disclose that linear phosphonitrilic chlorides represented by formula $Cl_3P(NPCl_2)_nNPCl_3^+ \ PCl_6^-$, wherein n is an integer of from 1 to 6, preferably 1, are effective as catalysts for polycondensation and equilibration of the low viscosity siloxane polymers. These catalysts are especially valuable for the production of silicone rubber and siloxane fluids with a low content of hydroxyl end groups. More recently, U.S. Pat. Nos. 4,888,405 and 5,008,229 (1991) (to Wacker Chemie) have disclosed new catalytic compositions containing phosphonitrile chlorides and/or reaction products of phosphonitrile chlorides with organopolysiloxanes and/or organosilanes, the latter also including a solubilizer and a halogen-free solvent. A recent patent (GB Patent 2,252,969 (1992)) (to Dow Corning) describes catalyst compounds of general formula: $Cl_3P(NPCl_2)_nNPCl_3^+ \ ECl_m^-$ where E is an element having an electronegativity value of from 1.2 to 2 such as Al, Sb, P, Sn, Zn and Fe.

In spite of the foregoing developments, there is a continuing search for catalysts which will improve activity in the polymerization of organosiloxanes. It is known that the application of standard linear phosphonitrilic chlorides (LPNC's) as catalysts for polycondensation of low molecular siloxanediols can produce a high molecular gum which does not contain cyclic oligosiloxanes and that the gum can be prepared in a short cycle time. The present work has shown that the physical mixture of high molecular weight organopolysiloxanes and low molecular weight siloxanes can be redistributed into linear polymers, which have an average number molecular weight, without formation of a significant amount of cyclic species. In addition, it has been discovered that compositions containing novel reaction products of linear phosphonitrile chlorides with compounds containing active protons with pKa values below 18 are active catalysts for polycondensation and redistribution of organosiloxane polymers. In particular, it has been found, for example, that novel products of reaction of 1 mol of LPNC of formula $$Cl_3P(NPCl_2)_nNPCl_3 \cdot PCl_6$$

with preferably 1 to 4 mols, of compounds containing active protons with pKa values below 18 yields very active catalysts for polycondensation and rearrangement of organosiloxanes. The solvents and low boiling products were removed from the system by vacuum at 80° C. over a period of 2 hours. The resulting light yellow residue is soluble in many organic solvents such as methylene chloride, methanol, ethers and low viscosity silicone oil. The chlorine analysis showed that this new composition contains significantly lower amounts of chlorine than the starting LPNC. The new chemical compositions described above were also tested as a catalyst for polycondensation and redistribution of organosiloxanes. The catalytic activity of this new catalyst was higher than the standard LCPN. The products of the polycondensation and redistribution of organosiloxane polymers do not contain oligomeric cyclic species. The development and use of such standard and new and improved catalysts for polycondensation and redistribution of organosiloxanes is the subject matter of the present invention.

OBJECTS OF THE INVENTION

It is a primary object of the present invention to provide new processes and catalysts for the polycondensation and redistribution of organosiloxanes.

It is another object of the invention to provide linear phosphazenes and derivatives of such as catalysts for polycondensation of low molecular siloxanediols to high molecular gums which do not contain cyclic oligosiloxanes and to do so in short cycle times.

It is a further object of the invention to provide for physical mixtures of high molecular weight organopolysiloxanes and low molecular weight siloxanes to be redistributed into linear polymers, which have an average molecular weight in between those of both starting materials without, at the same time, forming cyclic species.

SUMMARY OF THE INVENTION

These and other objects are provided in accordance with the present invention by preparing and using short-chain linear phosphazenes of Formulae (Ia) or I(b):

$$O(X)_{2-m}Y_mP\{NP(X)_2\}_nNP(X)_{3-q}(Y)_q \qquad (Ia)$$

$$O(X)_{2-m}Y_mP\{NP(X)_2\}_nN(H)P(O)(X)_{2-p}(Y)_p \qquad (Ib)$$

where n=0 or an integer from 1 to 8; m=0 or an integer of 1; p=0 or an integer of 1; q=0 or an integer of from 1 to 2; X=halogen; Y=OH, OR, O(O)CR, wherein R is alkyl or aryl, as catalysts for polycondensation and redistribution of organopolysiloxanes.

Also contemplated are reaction products of the linear compounds with compounds containing active protons with pKa values below 18, such as carboxylic acids, halogenoalkane carboxylic acids, sulfonic acids, alcohols, phenols and water.

Preferred species of the new catalysts have a low content of chlorine and comprise those of the Formulae (Ic), (Id) and I(e):

$$OCl_2P(NPCl_2)_nNPCl_2OH, \quad (Ic)$$

$$OCl_2P(NPCl_2)_nN(H)PCl_2O, \quad (Id)$$

$$OCl_2P(NPCl_2)_nNPCl_3, \quad (Ie)$$

where n is 0 or an integer of from 1 to 8, preferably from 1 to 3. Compounds of Formula (Ic), (Id) and (Ie) wherein n is 0 or 1 are soluble in halogen-free solvents, such as ethers, ketones, e.g., acetone, esters, e.g., ethyl acetate, aromatic hydrocarbons, e.g., toluene, mixtures of any of them, and the like.

Among the preferred embodiments are short-chain linear phosphazene catalysts (Ia), (Ib), (Ic), (Id) and (Ie) wherein each X group denotes a chlorine atom; those wherein each Y group denotes a hydroxyl group; those wherein m values can vary from 0 to 1; those wherein q values can vary from 0 to 2; those wherein p values can vary from 0 to 1.

Also contemplated by the present invention is a process comprising polycondensing a low molecular weight organopolysiloxanediol having an average degree of substitution of from 1.9 to 2.1 organic groups attached to silicon per silicon atom to a high molecular weight organopolysiloxane in a short cycle time without forming a substantial content of cyclics by using an effective catalytic amount of a short-chain linear phosphazene of the formulae as above defined; and such a process which also includes in the reaction mixture an oligoorganosiloxanol or a triorganosiloxy-terminated organosiloxane as a chain stopper.

In another major aspect, the present invention contemplates the use of a catalyst as above defined for redistributing organopolysiloxanes having an average degree of substitution of from 1.9 to 2.1 organic groups attached to silicon per silicon atom in the presence of low molecular weight triorganosiloxy-terminated organosiloxanes to produce low viscosity triorganosiloxy-terminated oils, especially those substantially free of an increased content of cyclic by-products.

Preferred embodiments of the processes of the invention include the step of deactivating the catalyst by heating the final product at temperature above 170° C., preferably at 200° C.; or deactivating the catalyst by treating the final product with basic nitrogen compounds like ammonia, amines, organosilazanes; or deactivating the catalyst by treating the final product with strong basic compounds like metal oxides, metal hydroxides, metal carbonates where the metal is selected from the mono, di- and trivalent metals like lithium, sodium, magnesium, calcium, barium, zinc and aluminum, organometallic compounds, such as butyl lithium, lithium bis(trimethylsilyl)amide, mixtures of any of them, or the like.

The present invention includes, among its preferred features, the synthesis of a new catalytic composition, with low content of halide, preferably chloride, which comprises products of reaction of phosphonitrile halides of formula $X_3P(NPX_2)_nNPX_3 \cdot EX_{v+1}$, where the n values can vary from 0 to 6, and E represents phosphorus or another element having an electronegativity of from 1 to 2 according to Pauling's scale, e.g., aluminum, antimony, iron, and the like, and v is the valence or oxidation state to balance, with compounds containing an active proton with pKa values below 18, such as carboxylic acids, halogenoalkane carboxylic acids, sulfonic acids, alcohols, phenols and water, preferably such catalytic compositions wherein each X group denotes a chlorine atom. Preferred preparation methods comprise addition of compounds containing active proton into a solution of phosphonitrile chlorides in methylene chloride and subsequent removing of low boiling materials, e.g., by addition of carboxylic acid into a solution of phosphonitrile chlorides in methylene chloride and subsequent removing of low boiling material. Also contemplated are the use of such catalytic compositions for polycondensation of low molecular weight organopolysiloxanediols having an average degree of substitution of from 1.9 to 2.1 organic groups attached to silicon per silicon atom; and the use of such compositions for the polycondensation of low molecular siloxanediols having an average degree of substitution of from 1.9 to 2.1 organic groups attached to silicon per silicon atom in the presence of oligoorganosiloxanols as a chain stopper; and the use of such catalytic compositions for the polycondensation and redistribution of organopolysiloxanediols having an average degree of substitution of from 1.9 to 2.1 organic groups attached to silicon per silicon atom in the presence of low molecular weight triorganosiloxy-terminated organosiloxanes as chain stoppers; as well as the use of such catalytic compositions for the redistribution of triorganosiloxy-terminated organopolysiloxanes having an average degree of substitution of from 1.9 to 2.1 organic groups attached to silicon per silicon atom in the presence of low molecular weight triorganosiloxy-terminated organosiloxanes to produce lower viscosity triorganosiloxy-terminated oils.

DETAILED DESCRIPTION OF THE INVENTION

The phosphazenes of this invention are linear low polymers, i.e., oligomers of the general formulae set forth above, and the derivatives mentioned above. Although the halogen X can be chloro, bromo, iodo, fluoro, and the like, it is preferred, that the halogen X is a chlorine atom. Phosphazenes with a value for n which is higher than 8 are less suitable as catalysts. Most preferred are the phosphazenes in which the value of n is from 0 to 3. It is sometimes difficult to separate the oligomeric phosphazenes having different n values and mixtures are often used. It is particularly preferred that the amount of phosphazene oligomer, in which n has a value of 1, is as high as possible as this gives the most active catalyst. Particularly preferred is a catalyst which exclusively consists of compounds according to the invention in which the value of n is 1.

The part of the catalyst designated Y is hydroxy, alkoxy, phenoxy, aryloxy, carboxyloxy, and the R groups can be alkyl or substituted alkyl groups, e.g., of from 1 to 18 carbon atoms, or aryl or substituted aryl groups of from 6 to 18 carbon atoms.

Linear short-chain phosphazene catalysts according to the invention may be made by reacting a phosphorus pentahalide, and an ammonium halide, sulfate, or other equivalent salt, and, if desired subsequently, the corresponding reagent: water, an alcohol, a phenol, a carboxylic acid or reactive derivative thereof, an organosiloxane, an organosilane, an organosilazane, a mixture of any of them, or the like. Preferably they are made by reacting in the presence of an aromatic hydrocarbon or more preferably of a chlorinated aliphatic or aromatic hydrocarbon, e.g. toluene, sym-tetrachloroethane, methylene chloride, or 1,2,4-trichlorobenzene, and the like, as inert solvent, the phosphorus pentahalide, e.g. phosphorus pentachloride, the ammonium salt, e.g. ammonium chloride or ammonium sulfate, and the selected optional reagent. Examples of suitable optional reagents are water, methyl alcohol, ethyl alcohol, t-butyl alcohol, n-octanol, 2-ethylhexanol, octadecanol-1, and the like, phenol, 4-ethyl phenol, 1 naphthol, and the like, formic acid, acetic acid, propionic acid, n-hexanoic acid, stearic acid, and the like, sulfur dioxide, octamethylcyclotetrasiloxane, hexamethyldisilazane, hexamethyldisiloxane, octamethyltetrasiloxane diol, mixtures of any of them, and the like. The reagents, phosphorus pentachloride and ammonium salts, may be contacted for any period of time but preferably a period which may vary from 1 to 10 hours. It is preferred to continue the reaction for a period in excess of 3 hours. It is preferred to react the reagents till a fair amount of the phosphazenes produced are oligomers with more than 2 units. Preferably the reaction conditions are adapted to provide a high level of linear trimers and tetramers. The yield of linear phosphazene halides versus cyclic phosphazene halides can be increased by using less than a stoichiometric amount of ammonium salt, which is the preferred method. In such preferred method from 0.9 to 0.05 mole, more preferably 0.6 to 0.2 mole of the selected ammonium salt is provided for each mole of phosphorus pentahalide.

Representative chlorinated aliphatic or aromatic hydrocarbons that are inert solvents and can be used in the present invention include symmetric tetrachloroethane, methylene chloride, monochlorobenzene, o-dichlorobenzene and 1,2,4-trichlorobenzene. The amount of chlorinated hydrocarbon used as solvent seems not to be critical provided a sufficient amount is used to dissolve at least a portion of the solid reactants, i.e. phosphorus pentahalide and ammonium halide, ammonium sulfate, and the like. Of course the reaction rate improves substantially when a significant portion of the solid reactants is in solution. The use of large quantities of solvent, however, is not recommended because of the necessity of subsequent removal of the solvent from the reaction product. The manner of recovering the desired modified phosphazene polymeric composition is not critical. If any solid material is present in the reaction mixture it may be removed by any conventional method, e.g. hot filtration, decantation, centrifugation etc. The volatile materials e.g. the solvent, may be also removed by conventional methods, e.g. distillation. The preferred methods of recovering the catalyst include distillation, crystallization, or the addition of a solvent in which only the most preferred compounds are insoluble, e.g. hexane, petroleum ether, etc. The preferred compounds can then be filtered off. The catalyst according to the invention can be conveniently stored neat or in a solvent, preferably under a blanket of nitrogen. The invention accordingly also includes catalyst compositions which comprise a catalyst according to the invention. The other parts of the composition may include a solvent, a carrier, a support and some unreacted materials which were used for making the catalyst. It is also possible that some compounds according to the formulae above are present but wherein the value of n is larger than 8. Preferably the amount of such compounds is kept to a minimum. Concentrations of the catalyst in such compositions may range from 1 to 50% by weight. Preferably from 5 to 20% because this facilitates its use in polymerization processes.

The catalysts of the invention are useful for the polymerization of organosiloxanes. The invention accordingly also provides the use of linear phosphazene catalysts of formulae (Ia), (Ib), (Ic), (Id) and (Ie), as defined above, in the process of polymerizing organosiloxanes. They are particularly useful as condensation catalysts but are also suitable as redistribution catalysts. Thus they will be useful for a process of making organopolysiloxanes having units of the general formula (II)

wherein $R^1$ denotes a hydrogen atom, a hydrocarbon group having from 1 to 18 carbon atoms, a substituted hydrocarbon group having from 1 to 18 carbon atoms and a has on average a value of from 1.8 to 2.2. $R^1$ substituents may be alkyl, e.g. methyl, ethyl, propyl, isobutyl, hexyl, dodecyl or octadecyl, alkenyl, e.g. vinyl, allyl, butenyl, hexenyl or decenyl, alkynyl, e.g. propargyl, aryl, e.g. phenyl, aralkyl, e.g. benzyl, alkaryl, e.g. tolyl or xylyl, substituted groups, e.g. trifluoropropyl, chloropropyl or chlorophenyl. Preferably at least 80% of all $R^1$ groups are alkyl or aryl groups, more preferably methyl groups. Most preferably substantially all $R^1$ groups are alkyl or aryl groups, especially methyl groups. The organopolysiloxanes are preferably those in which the value of a is 2 for practically all units, except for the endblocking units, and the siloxanes are substantially linear polymers of the general formula (III)

wherein $R^1$ is as defined above, $R^2$ is a group $R^1$, or alkoxy or aryloxy, or a hydroxyl group and r is an integer. It is, however, also possible that small amounts of units wherein the value of a denotes 0 or 1 are present. Polymers with such units in the chain would have a small amount of branching present. Preferably $R^2$ denotes a hydroxyl group or an alkyl or aryl group, e.g methyl or phenyl. The viscosity of the organopolysiloxanes which may be produced by the process using a catalyst according to the present invention may be in the range of from 50 to many millions mm²/s, depending on the reaction conditions and raw materials used in the method of the invention. Suitable organosiloxanes for use as reagents in a polymerization process in which the catalysts of the invention are used include polydiorganosiloxanes having terminal hydroxydiorganosiloxane units, e.g. hydroxyldimethylsiloxane endblocked polydimethylsiloxanes, hydroxyldimethylsiloxane endblocked polydimethyl polymethylphenyl siloxane copolymers, triorganosiloxane endblocked polydimethylsiloxanes, e.g. trimethylsiloxane endblocked polydimethylsiloxanes and cyclic polydiorganosiloxanes, e.g. octamethylcyclotetrasiloxanes.

The catalysts of the invention may be used at a concentration of from 1 to 1000 ppm by weight based on the total weight of the organosiloxanes used as reagents in a polymerization process. Preferably from 5 to 150 ppm by weight are used, most preferably from 5 to 50 ppm. The amount of catalyst used in the method of the invention may be reduced when the temperature at which the organosilicon compounds and the catalyst are contacted is increased. The method of the invention may conveniently be carried out at room temperature. The temperature may also be as high as 190° C., or as low as 0° C. Preferably, however, the temperature range is from 20° to 160° C., most preferably from 50° to 120° C. It is preferred to operate under vacuum; vacuum increases the reaction rate of condensation significantly.

Catalysts according to the invention may be neutralized at the end of the polymerization reaction in order to stabilize the reaction product, e.g. in respect of its viscosity. The neutralization may be done at any stage of the polymerization process, e.g. as soon as the desired viscosity of the organopolysiloxanes is reached. Neutralization agents for the catalysts are alkaline materials, preferably lightly alkaline materials. Examples of suitable neutralization agents are diethylamine, propylamine, ammonia and hexamethyldisilazane.

It has been found that short-chain linear oligophosphazenes of formulae (Ia), (Ib), (Ic), (Id) and (Ie) are very effective catalysts for polycondensation and redistribution of organosiloxanes. The catalytic activity of these new catalysts in the polycondensation and redistribution of organosiloxane polymers are comparable to linear phosphonitrilic chlorides. The products of the polycondensation and redistribution of organosiloxane polymers do not contain more than trace amounts, i.e., more than 2.0% by weight, of oligomeric cyclic species.

It has further been found that reaction of 1 mol of linear phosphonitrilic chlorides (LPNC) of the formula $Cl_3P(NPCl_2)_nNPCl_3$. $PCl_6$ with 1 mol of low molecular weight siloxanediol (PS 341, MW=4,000 Hüls), and 1 mol of nonamethyltetrasiloxane-1-ol at room temperature in methylene chloride yields in few minutes a low viscosity two phase mixture which contains LPNC, siloxane polymers and water. The methylene chloride, water, HCl and siloxane materials were removed from the system by vacuum at 80° C. over 2 hours. The resulting yellow residue is soluble in many organic solvents such as methylene chloride, methanol, ethers and low viscosity silicone oil. The chlorine analysis showed that this new catalyst contains significantly lower amounts of chlorine—only 57.5% compared to 80% in the starting LPNC.

The new chemical composition described above was tested as a catalyst for polycondensation and redistribution of organosiloxanes, as will be set forth in the detailed examples which follow. The catalytic activity of this new catalyst is even higher than standard LPNC. The high molecular weight product of polycondensation of low molecular weight siloxanediols does not contain increased contents of oligomeric cyclic species. Interestingly, the catalyst is active in the temperature range from 0° C. to 160° C. Above 160° C. the activity of this particular catalyst dramatically decreases. At 200° C. this new catalyst is inactive. This behavior allows for a deactivation of the catalyst in the final product by heating to 200° C. for short periods of time. A silicone high molecular weight gum prepared using the new catalyst at 120° C. and then heated at 200° C. for 5 minutes exhibits high thermal stability. The resulting silicone material passes standard GE Silicones E-68 test.

DESCRIPTION OF THE PREFERRED EMBODIMENTS

The following examples illustrate the present invention but the claims are not intended to be limited thereto. Unless otherwise specified, all parts are by weight. The Test Method designated E-68 is carried out as follows: The test conditions consist of placing a 1 gram sample in a metal cup and placing the cup in a heated chamber at 350° C. A stream of nitrogen which has been saturated with water at room temperature and subsequently heated to 350° C. is blown over the sample in the oven. After 15 minutes, the sample is removed and measured for weight loss. This test measures the thermal stability of the polymer, and the temperature is chosen to be just at the point where a very stable polydimethylsiloxane begins to decompose thermally. Low weight losses in this test indicate that the polymer under test does not contain an active equilibration catalyst.

EXAMPLE 1

Preparation of $OCl_2PNPCl_3$

A 100 ml flask was charged with 20.8 g (0.1 mol) of phosphorus pentachloride, 2.93 g (0,022 mol) of ammonium sulfate and 50 ml of symtetrachloroethane. The mixture was stirred and refluxed over 1 hour. After the reaction was over, the solvent was removed and the product was purified by vacuum distillation (b.p. 110°–115° C./0.1 mm Hg). The yield of the title product as light yellow crystals was 12 g.

EXAMPLE 2

Preparation of $OCl_2PNPCl_2NPCl_3$

A 100 ml flask was charged with 13.5 g (0.05 mol) of the title compound of Example 1, 11.6 ml (0.055 mol) of $HN(Si(CH_3)_3)_2$ and 20 ml of methylene chloride. The mixture was stirred and refluxed over 12 hours. After the reaction was over, 10.3 g (0.05 mol) of $PCl_5$ was added, and the reaction mixture was refluxed for an additional 12 hrs. The solvent was removed by rotavaporation and product was purified by vacuum distillation (b.p. 170°–175° C./0.1 mm Hg). The yield of the title product as light yellow liquid was 8 g.

EXAMPLE 3

Preparation of $OCl_2PNPCl_2NPCl_2OH$ by Hydrolysis of the Product of Example 2

A 100 ml flask was charged with 0.5 g (0.0013 mol) of the product of Example 2, and 5 ml of methylene chloride. Water (23.3 microliters, 0.0013 mol) was added. The mixture was stirred over 2 hours. After the reaction was over, solvent was removed by rotavaporation. The yield of the named product as a yellow liquid was 0.36 g.

EXAMPLE 4

Polycondensation of Polydimethylsiloxanediol with Catalyst of Example 1 at Room Temperature A 50 ml beaker was charged with 10 g of PS 341 (MW=4,000 polydimethylsiloxanediol, Hüls) and 10 microliters of 3% solution of the catalyst of Example 1 in methylene chloride. Instead of methylene chloride, ethyl acetate can be used with the same results. The mixture was stirred for 2 minutes. After 2 minutes a turbid mixture was formed. This blend was left at room temperature (23° C.) over 24 hours. After 2 hours a clear high molecular polysiloxane was formed on the top of the cloudy mixture. With time the layer of clear high molecular weight polysiloxane increased and in 24 hours it reached the bottom of the beaker.

EXAMPLE 5

Polycondensation of Polydimethylsiloxanediol with Catalyst of Example 1 in the Presence of Dodecamethyltetrasiloxane Chain Stopper in a Haake Mixer at 120° C.

A Haake Mixer was charged with 50 g of PS 343 (MW = 26,000 polydimethylsiloxanediol, Hüls) and 0.0196 g of dodecamethyltetrasiloxane as a chain stopper. The mixer was heated to 120° C. After reaching the desired temperature, 18 ppm (30 microliter of 3% solution) of the catalyst of Example 1 in methylene chloride was added. Instead of methylene chloride, ethyl acetate can be used with the same results. The polycondensation was followed by monitoring the torque. After 40 minutes of reaction, the torque reached a maximum reading and did not change with time. The resulting high molecular siloxane gum had a molecular weight MW = 400,000 and did not contain any oligomeric cyclic species.

EXAMPLE 6

Polycondensation of Polydimethylsiloxanediol with Catalyst of Example 2 in the Presence of Dodecamethyltetrasiloxane Chain Stopper in a Haake Mixer at 120° C.

A Haake Mixer was charged with 50 g of PS 343 (MW = 26,000 polydimethylsiloxanediol, Hüls) and 0.0196 g of dodecamethyltetrasiloxane as a chain stopper. The mixer was heated to 120° C. After reaching the desired temperature, 18 ppm (30 microliters of 3% solution) of the Catalyst of Example 2 in methylene chloride was added. Instead of methylene chloride, ethyl acetate can be used with the same results. The polycondensation was followed by monitoring the torque. After 40 minutes of reaction the torque reached a maximum reading and did not change with time. The resulting high molecular siloxane gum had molecular weight MW = 400,000 and did not contain any oligomeric cyclic species.

EXAMPLE 7

Synthesis of Triorganosilylterminated Low Molecular Weight Oils with Catalyst of Example 3 at 90° C.

A 250 ml flask equipped with mechanical stirrer, condenser and vacuum outlet was charged with 10 g of MW = 80,000 polydimethylsiloxane and 1 g of hexamethyldisiloxane. The flask was heated to 90° C. After reaching the desired temperature, 18 ppm (30 microliters of 3% solution in methylene chloride ) of the catalyst of Example 3 was added. Very fast loss of viscosity was observed. After 20 minutes the reaction was stopped by quenching the catalyst with hexamethyldisilazane. The resulting trimethylterminated silicone oil had a molecular weight MW = 1000 and did not contain significant amount of oligomeric cyclic species.

EXAMPLE 8

Preparation of Catalyst Comprising Reaction Product of Linear Phosphonitrilic Chlorides, Siloxanediol and Tetrasiloxaneol (a) Preparation of Linear Phosphonitrilic Chlorides A 100 ml flask was charged with 20.5 g (0.5 mol) of phosphorus pentachloride, 2.7 g (0.05 mol) of ammonium chloride and 50 g of tetrachloroethane. The mixture was stirred and refluxed for 8 hours. After the reaction was over, the reaction mixture was poured into petroleum ether. The precipitate was dissolved in methylene chloride and reprecipitated with petroleum ether. After removing traces of solvent under vacuum, 14 g of light yellow crystals of the title product (LPNC) were obtained.

(b) Preparation of Catalyst

A 50 ml flask was charged with 4.0 g of PS 341 (MW = 4,000 polydimethylsiloxanediol Hüls) organosiloxanediol and 0.8 g of nonamethyltetrasiloxane-1-ol and 10 ml of methylene chloride. Then 1 g of LPNC in 10 ml of methylene chloride was added at once at room temperature. After a few seconds a large amount of water was formed. The resulting turbid two phase mixture was stirred for 15 minutes. The solvents and organosilicone materials were removed from the system by heating to 80° C. under reduced pressure (0.05 mm Hg) for 2 hours to afford 0.7 g of light yellow catalytically-active viscous oil, which was dissolved in 23 ml of methylene chloride.

EXAMPLE 9

Polycondensation of Polydimethylsiloxanediol with Catalyst of Example 8b

A 50 ml beaker was charged with 10 g of PS 343 (MW = 26,000 polydimethylsiloxanediol, Hüls), and 10 microliters of a 3% solution of catalyst of Example 8b in methylene chloride. The mixture was stirred for 2 minutes. After 2 minutes a turbid mixture was formed. This blend was left at room temperature over 24 hours. After 2 hours a clear high molecular polysiloxane was formed on the top of the cloudy mixture. With time a layer of clear high molecular weight polysiloxane was becoming wider and in 24 hours it reached the bottom of the beaker.

EXAMPLE 10

Polycondensation of Polydimethylsiloxanediol with Catalyst of Example 8b in a Haake Mixer at 120° C.

A Haake Mixer was charged with 50 g of PS 343 (MW = 26,000 polydimethylsiloxanediol, Hüls). The mixer was heated to 120° C. After reaching the indicated temperature 18 ppm (30 microliters of a 3% solution in methylene chloride) of catalyst of Example 8b was added. The polycondensation was followed by monitoring the torque. After 40 minutes of reaction the torque reached a maximum reading and did not change with time. The resulting high molecular siloxane gum had a molecular weight MW = 900,000 and did not contain any oligomeric cyclic species.

EXAMPLE 11

Polycondensation of Polydimethylsiloxanediol with Catalyst of Example 8b in the Presence of Nonamethyltetrasiloxanol Chain Stopper in a Haake Mixer at 120° C.

A Haake Mixer was charged with 50 g of PS 343 (MW = 26,000 polydimethylsiloxanediol, Hüls) and 0.026 g of nonamethyltetresiloxanol as a chain stopper. The mixer was heated to 120° C. After reaching desired temperature 18 ppm (30 microliters of 3% solution in methylene chloride) of catalyst of Example 8b was added. The polycondensation was followed by monitoring the torque. After 40 minutes of reaction the torque reached a maximum reading and did not change with time. The resulting high molecular siloxane gum had a molecular weight MW=420,000 and did not contain any oligomeric cyclic species.

EXAMPLE 12

Polycondensation of Polydimethylsiloxanediol with Catalyst of Example 8b in the Presence of Dodecamethyltetrasiloxane Chain Stopper in a Haake Mixer at 120° C.

A Haake Mixer was charged with 50 g of PS 343 (MW=26,000 polydimethylsiloxanediol, Hüls) and 0.0196 g of dodecamethyltetrasiloxane as a chain stopper. The mixer was heated to 120° C. After reaching the desired temperature 18 ppm (30 microliters of 3% solution in methylene chloride) of Example 8b catalyst was added. The polycondensation was followed by monitoring the torque. After 40 minutes of reaction the torque reached a maximum reading and did not change with time. The resulting high molecular weight siloxane gum had a molecular weight of MW=430,000 and did not contain any oligomeric cyclic species.

EXAMPLE 13

Deactivation of Polycondensed Siloxane Material of Example 11 by Introduction of Hexamethyldisilazane To the polymer from Example 11 1 microliter of hexamethyldisilazane was added, and resulting mixture was mixed for additional 5 minutes at 120° C. The resulting polymer has a high thermal stability (passed E-68 GE Silicones test).

EXAMPLE 14

Deactivation of Polycondensed Siloxane Material of Example 11 by Heating to 200° C.

The polymer from Example 11 was heated to 200° C. for 5 minutes with mixing. The resulting polymer has high thermal stability (passed E-68 GE Silicones test).

EXAMPLE 15

Deactivation of Polycondensed Siloxane Material of Example 12 by Introduction of Hexamethyldisilazane To the polymer from Example 12 1 microliter of hexamethyldisilazane was added, and the resulting mixture was mixed for an additional 5 minutes at 120° C. The resulting polymer had high thermal stability (passed E-68 GE Silicones test).

EXAMPLE 16

Deactivation of Polycondensed Siloxane Material of Example 12 by Heating to 200° C.

The polymer from Example 12 was heated to 200° C. for 5 minutes with mixing. The resulting polymer had high thermal stability (passed E-68 GE Silicones test).

EXAMPLE 17

Synthesis of Triorgano-terminated low Molecular Weight Siloxane Oils

A 250 ml flask equipped with mechanical stirrer, condenser and vacuum outlet was charged with 50 g of PS 343 (MW=26,000 polydimethylsiloxanediol, Hüls) and 7.0 g of dodecamethyltetrasiloxane as a chain stopper. Mixer was heated to 90° C. After reaching the desired temperature 18 ppm (30 microliters of 3% solution in methylene chloride) of the catalyst of Example 8b was added. A very fast polycondensation was observed (considerable foam was formed and water was condensed in vacuum trap). After 30 minutes of reaction, the reaction was stopped by quenching the catalyst with hexamethyldisilazane. The resulting trimethyl-terminated silicone oil had a molecular weight, MW=3000 and did not contain any significant amounts of oligomeric cyclic species.

EXAMPLE 18

Preparation of Catalyst Comprising Reaction Product of Linear Phosphonitrilic Chlorides and Acetic Acid (a) Preparation of Linear Phosphonitrilic Chlorides The procedure of Example 8, Step (a) is repeated to provide the title compound.

(b) Preparation of Catalytic Composition

A 50 ml flask was charged with 1 g (0.00154 mol) of LPNC from Step (a) and 20 ml of methylene chloride. Then 0.185 g (0.00308 mol) of acetic acid was added at once at room temperature. The resulting mixture was stirred over 2 hours. During that time, evolution of HCl was observed. After 2 hours the solvent and low boiling material were removed from the system by heating to 80° C. under reduced pressure (0.05 mm Hg) for 2 hours to afford 0.7 g of light yellow viscous oil, which was dissolved in 14 ml of methylene chloride. This solution was used as a catalytic composition in following examples.

EXAMPLE 19

Polycondensation of Polydimethylsiloxanediol at Room Temperature

A 50 ml beaker was charged with 10 g of polydimethylsiloxanediol (PS 341, MW=4,000, Hüls) and 10 microliters of the acetic acid-modified catalytic composition of Example 18. The mixture was stirred for 2 minutes. After 2 minutes a turbid mixture was formed. This blend was left at room temperature over 24 hours. After 2 hours a clear high molecular weight polysiloxane was formed on the top of the cloudy mixture. With time the layer of clear high molecular weight polysiloxane increased and in 24 hours it reached the bottom of the beaker.

EXAMPLE 20

Polycondensation of Polydimethylsiloxanediol in the Presence of Dodecamethyltetrasiloxane in a Haake Mixer A Haake Mixer was charged with 50 g of polydimethylsiloxanediol (PS 343, MW=26,000, Hüls) and 0.0196 g of dodecamethyltetrasiloxane as a chain stopper. The mixer was heated to 120° C. After reaching the desired temperature, 18 microliters of the catalytic composition of Example 18 was added. The polycondensation was followed by monitoring the torque. After 30 minutes of reaction, the torque reached a maximum reading and did not change with time. The resulting high molecular siloxane gum had a molecular weight MW=400,000 and did not contain any oligomeric cyclic species.

EXAMPLE 21

Synthesis of Triorganosilyl-terminated Low Molecular Weight Siloxane Oils

A 250 ml flask equipped with mechanical stirrer, condenser and vacuum outlet was charged with 40 g of polydimethylsiloxanediol (PS 341, MW=4,000, Hüls) and 0.154 g (4×10 mol) of dodecamethyltetrasiloxane. The flask was heated to 90° C. After reaching the specified temperature, 20 microliters of the catalytic composition of Example 18 was added. The resulting mixture was stirred under vacuum (0.1 mm Hg). A very fast polycondensation occurred. After 5 minutes of reaction, a high molecular weight polydimethylsiloxane (PDMS) was formed (MW=90,000). At this point, 1 g (0.006 mol) of hexamethyldisiloxane was added. The resulting mixture was stirred at 90° C. A very fast loss of viscosity was observed. After 20 minutes the reaction was stopped by quenching the catalyst with hexamethyldisilazane, The resulting trimethylsilylterminated silicone oil has a MW=7,000 and does not contain a significant amount of oligomeric cyclic species.

EXAMPLE 22

Synthesis of Vinyldimethylterminated Siloxane Oil in the Presence of Short Chain Phosphazanes A 250 ml flask equipped with mechanical stirrer, condenser and vacuum outlet was charged with 50 g of polydimethylsiloxanediol (PS 341, MW=4,000, Hüls) and 5 g of vinyldimethylterminated siloxane oil (MW=4,200) as a chain stopper. The mixture was heated to 90° C. After reaching the desired temperature, 20 ppm (22 microliters of a 5% solution in methylene chloride) of the acetic acid modified catalyst (from Example 18 was added). The reaction mixture was stirred under a vacuum of 0.1 mm Hg. Very fast polycondensation was observed (considerable foam was formed and water was condensed in vacuum trap). After 2 minutes of reaction a high molecular weight polymer was formed (viscosity >200,000 cSt). In the next 8 minutes the viscosity of the reaction mixture went down to reach 2,600 cSt after 10 minutes. Addition of an extra 20 ppm of catalyst at this point did not change the viscosity of the resulting polymer. The resulting vinyldimethyl-terminated silicone oil has MW=50,000 and contains less than 1% of oligomeric cyclic species.

EXAMPLE 23

Synthesis of Low Molecular Weight Vinyldimethyl-terminated Siloxane Oil in the Presence of Short-chain Phosphazanes A 250 ml flask equipped with mechanical stirrer, condenser and vacuum outlet was charged with 50 g of vinyldimethyl-terminated siloxane oil (MW=50,000) from Example 21 and 4.25 g of divinyltetramethyldisiloxane as a chain stopper. The mixture was heated to 90° C., after reaching desired temperature a 20 ppm (22 microliters of a 5% solution in methylene chloride) of catalyst (from example 18) was added. The reaction mixture was stirred at 90° C. A fast loss of viscosity was observed. After 20 minutes of reaction the viscosity of the polymer went down to 31 cSt. Addition of an extra 20 ppm of catalyst at this point did not change viscosity of resulting polymer. The resulting vinyldimethyl-terminated silicone oil has MW=4,200 and contains a small amount of oligomeric cyclic species.

EXAMPLE 24

Synthesis of Vinyldimethyl-terminated Siloxane Oil in the Presence of Short-chain Phosphazanes A 250 ml flask equipped with mechanical stirrer, condenser and vacuum outlet was charged with 50 g of polydimethylsiloxanediol (PS 341, MW=4,000, Hüls) and 3 g of vinyldimethyl-terminated siloxane oil (MW=4,200) as a chain stopper. The mixture was heated to 90° C. After reaching the specified temperature a 20 ppm (12 microliters of 9% solution in ethyl acetate) of catalyst (from Example 1) was added. The reaction mixture was stirred under a vacuum of 0.1 mm Hg. A very fast polycondensation was observed (considerable foam was formed and water was condensed in the vacuum trap). After a few minutes of reaction a high molecular weight polymer was formed (viscosity>100,000 cSt) In 20 minutes, the viscosity went down to reach 40,000 cSt). At this point an extra 12 microliters of catalyst was added. In the next 2 hours, the viscosity of the reaction mixture went down to reach finally 18,000 cSt.

EXAMPLE 25

Synthesis of Vinyldimethyl-terminated Siloxane Oil in the Presence of Short-chain Phosphazanes A 250 ml flask equipped with mechanical stirrer, condenser and vacuum outlet was charged with 50 g of polydimethylsiloxanediol (PS 341, MW=4,000, Hüls) and 3 g of vinyldimethylterminated siloxane oil (MW=4,200) as a chain stopper. The mixture was heated to 90° C. After reaching the specified temperature, 28 ppm (17 microliters of 9% solution in ethyl acetate) of catalyst (from Example 2) was added. The reaction mixture was stirred under vacuum of 0.1 mm Hg. A very fast polycondensation was observed (considerable foam was formed and water was condensed in the vacuum trap). After a few minutes of reaction a high molecular weight polymer was formed (viscosity>100,000 cSt). In 10 minutes the viscosity went down to 23,000 cSt. After an additional 50 minutes the viscosity of the polymer reached 17,200 cSt. At this point an extra 17 microliters of catalyst was added. In the next 2 hours the viscosity of reaction mixture went down to reach a final viscosity of 15,500 cSt.

The above-mentioned patents, publications and Test Methods are incorporated herein by reference.

Many variations of the invention will suggest themselves to those skilled in this art in light of the above, detailed description. All such obvious modifications are within the full intended scope of the appended claims.

I claim:

1. A catalyst for polycondensation and redistribution comprises reaction product of a short-chain linear phosphazene of the general Formula (Ia) or (Ib):

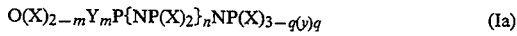

$$O(X)_{2-m}Y_mP\{NP(X)_2\}_nNP(X)_{3-q(y)}q \qquad (Ia)$$

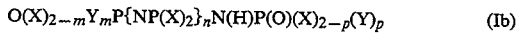

$$O(X)_{2-m}Y_mP\{NP(X)_2\}_nN(H)P(O)(X)_{2-p}(Y)_p \qquad (Ib)$$

where n=0 or an integer from 1 to 8; m=0 or an integer of 1; p=0 or an integer of 1; q =0 or an integer of from 1 to 2; X=halogen; Y=OH, OR, O(O)CR, wherein R is alkyl or aryl, with at least one compound containing at least one active proton with a pKa values below 18.

2. The catalyst as defined in claim 1 wherein said compound is selected from a carboxylic acid, a halogenoalkanecarboxylic acid, a sulfonic acid, an alcohol, a phenol, water or a mixture of any of the foregoing.

3. The catalyst of claim 1, wherein n is from 1 to 3.

4. The catalyst of claim 1, wherein each X group denotes a chlorine atom.

5. The catalyst of claim 1, wherein each Y group denotes a hydroxyl group.

6. The catalyst of claim 1, wherein m is 0 or 1.

7. The catalyst of claim 1, wherein q is 0 or an integer of from 1 to 2.

8. The catalyst of claim 1, wherein p is 0, 1 or 2.

9. A process for the polycondensation of low molecular weight organopolysiloxanediols having an average degree of substitution of from 1.9 to 2.1 organic groups attached to silicon per silicon atom, said process comprising carrying out said polycondensation in the presence of an effective catalytic amount of a phosphazene compound of the general formula (Ia) or (Ib):

$$O(X)_{2-m}Y_mP\{NP(X)_2\}_nNP(X)_{3-q}(Y)_q \quad \text{(Ia)}$$

$$O(X)_{2-m}Y_mP\{NP(X)_2\}_nN(H)P(O)(X)_{2-p}(Y)_p \quad \text{(Ib)}$$

where n=0 or an integer from 1 to 8; m=0 or an integer of 1; p=0 or an integer of 1; q =0 or an integer of from 1 to 2; X=halogen; Y=OH, OR, O(O)CR, wherein R is alkyl or aryl.

10. A process for the polycondensation of low molecular weight organopolysiloxanediols having an average degree of substitution of from 1.9 to 2.1 organic groups attached to silicon per silicon atom, said process comprising carrying out said polycondensation in the presence of an effective catalytic amount of a phosphazene compound of the general formula (Ic), (Id) or (Ie):

$$OCl_2P(NPCl_2)_nNPCl_2OH, \quad \text{(Ic)}$$

$$OCl_2P(NPCl_2)_nN(H)PCl_2O, \quad \text{(Id)}$$

$$OCl_2P(NPCl_2)_nNPCl_3, \quad \text{(Ie)}$$

where n is 0 or an integer of from 1 to 8.

11. A process as defined in claim 9 wherein the polycondensation is carried out in the presence of an effective chain-stopping amount of an oligoorganosiloxanol.

12. The process of claim 9, wherein the reaction is carried out in the presence of an effective chain-stopping amount of a low molecular weight triorganosiloxy-terminated organosiloxane.

13. The process of claim 10, wherein the reaction is carried out in the presence of an effective chain-stopping amount of a low molecular weight triorganosiloxy-terminated organosiloxane.

14. The process of claim 12, wherein the reaction is carried out in the presence of an effective chain-stopping amount of a low molecular weight triorganosiloxy-terminated organosiloxane so as to produce low viscosity triorganosiloxy-terminated oils.

15. The process of claim 13, wherein the reaction is carried out in the presence of an effective chain-stopping amount of a low molecular weight triorganosiloxy-terminated organosiloxane so as to produce low viscosity triorganosiloxy-terminated oils.

16. A process for deactivating after polycondensation or redistribution a catalyst comprising a phosphazene of the general formula (Ia) or (Ib):

$$O(X)_{2-m}Y_mP\{NP(X)_2\}_nNP(X)_{3-q}(Y)_q \quad \text{(Ia)}$$

$$O(X)_{2-m}Y_mP\{NP(X)_2\}_nN(H)P(O)(X)_{2-p}(Y)_p \quad \text{(Ib)}$$

where n=0 or an integer from 1 to 8; m=0 or an integer of 1; p=0 or an integer of 1; q =0 or an integer of from 1 to 2; X=halogen; Y=OH, OR, O(O)CR, Wherein R is alkyl or aryl, said process comprising heating the final product at temperature above 170° C. for a time sufficient to deactivate said catalyst and thereby to thermally-stabilize said final product.

17. A process for deactivating after polycondensation or redistribution a catalyst comprising a phosphazene of the general formula (Ia) or Ib):

$$O(X)_{2-m}Y_mP\{NP(X)_2\}_nNP(X)_{3-q}(Y)_q \quad \text{(Ia)}$$

$$O(X)_{2-m}Y_mP\{NP(X)_2\}_nN(H)P(O)(X)_{2-p}(Y)_p \quad \text{(Ib)}$$

where n=0 or an integer from 1 to 8; m=0 or an integer of 1; p=0 or an integer of 1; q=0 or an integer of from 1 to 2; X=halogen; Y=OH, OR, O(O)CR, wherein, R is alkyl or aryl, said process comprising heating the final product with a basic nitrogen compound selected from ammonia, amines, organosilazanes, mixtures thereof and the like, for a time sufficient to deactivate said catalyst and thereby to thermally-stabilize said final product.

18. A process for deactivating after polycondensation or redistribution a catalyst comprising a phosphazene of the general formula (Ia) or (Ib):

$$O(X)_{2-m}Y_mP\{NP(X)_2\}_nNP(X)_{3-q}(Y)_q \quad \text{(Ia)}$$

$$O(X)_{2-m}Y_mP\{NP(X)_2\}_nN(H)P(O)(X)_{2-p}(Y)_p \quad \text{(Ib)}$$

where n=0 or an integer from 1 to 8; m=0 or an integer of 1; p=0 or an integer of 1; q =0 or an integer of from 1 to 2; X=halogen; Y=OH, OR, O(O)CR, wherein R is alkyl or aryl, said process comprising heating the final product with a strong basic compound selected from a metal oxide, a metal hydroxide, a metal carbonate, where the metal is selected from mono-, di- and trivalent metals comprising lithium, sodium, magnesium, calcium, barium, zinc and aluminum, butyllithium, lithium bis(trimethylsilyl)amide, or a mixture of any of them, for a time sufficient to deactivate said catalyst and thereby to thermally-stabilize said final product.

19. A process for the preparation of a catalytic phosphazene composition, with low content of chlorine, which comprises reaction of a phosphonitrile halide of formula:

$$X_3P(NPX_2)_nNPX_3 \cdot EX_{v+1},$$

where the n values can vary from 0 to 6, and E represents phosphorus or another element having an electronegativity of from 1 to 2 according to Pauling's scale, e.g., aluminum, antimony, iron, and v is the valence or oxidation state to balance, with a compound containing an active proton and having a pKa value below 18 until formation of a catalytic composition having higher catalytic activity is substantially complete.

20. A process as defined in claim 19, wherein the compound containing an active proton is selected from a carboxylic acid, a halogenoalkane carboxylic acid, a sulfonic acid, an alcohol, a phenol, water or a mixture of any of the foregoing.

21. A process as defined in claim 20 wherein each X group denotes a chlorine atom.

22. A process as defined in claim 20 which comprises adding said compound containing an active proton into a solution of phosphonitrile chlorides in methylene chloride and subsequently removing low boiling materials.

23. A process as defined in claim 22 which comprises adding a carboxylic acid to a solution of phosphonitrile chlorides in methylene chloride and subsequently removing low boiling materials.

* * * * *